United States Patent [19]
Magarian et al.

[11] Patent Number: 5,397,802
[45] Date of Patent: Mar. 14, 1995

[54] GEM-DICHLOROCYCLOPROPANES AS ANTITUMOR AGENTS

[75] Inventors: Robert A. Magarian; Joseph T. Pento, both of Norman; May T. Griffin, Oklahoma City, all of Okla.

[73] Assignee: Research Corporation Technologies, Inc., Tucson, Ariz.

[21] Appl. No.: 20,922

[22] Filed: Feb. 22, 1993

Related U.S. Application Data

[63] Continuation-in-part of Ser. No. 812,246, Dec. 19, 1991, abandoned, which is a continuation-in-part of Ser. No. 432,564, Nov. 6, 1989, Pat. No. 5,098,903, which is a continuation-in-part of Ser. No. 98,945, Sep. 21, 1987, Pat. No. 4,879,315, which is a continuation-in-part of Ser. No. 363,429, Mar. 30, 1982, abandoned, which is a continuation-in-part of Ser. No. 166,255, Jul. 7, 1980, abandoned, which is a continuation-in-part of Ser. No. 128,040, Mar. 7, 1980, abandoned.

[51] Int. Cl.$^6$ ............................................. A01N 37/02
[52] U.S. Cl. .................................. 514/546; 514/717; 514/736; 560/130; 568/635; 568/639; 568/647; 568/774; 568/775; 568/807
[58] Field of Search ................ 560/130; 568/635, 639, 568/647, 774, 775, 807; 574/546, 717, 736

[56] References Cited

PUBLICATIONS

Madeddu et al., "A New Method for Evaluating the Inhibiting Potency of Antiestrogens on Breast Cancer Cell Lines", *Anticancer Research*, 6: 11–16, (1986).
Griffin et al., "Synthesis and Biological Evaluation of a Series of Gem–Dichlorocyclopropanes as Antitumor Agents", *Anti–Cancer Drug Design*, 7: 49–66, (1992).
Hausser et al., *J. Org. Chem.*, 37:4087–4090, (1972).
Magarian et al., *J. Pharmaceutical Sciences*, 61: 1216–1219, (1972).
Magarian et al, *J. Pharmaceutical Sciences*, 64:1626–1632, (1975).

*Primary Examiner*—José G. Dees
*Assistant Examiner*—Dwayne C. Jones
*Attorney, Agent, or Firm*—Dunlap Codding

[57] ABSTRACT

Gem-Dichlorocyclopropanes (Analog II derivatives) which demonstrate antiproliferative activity toward MCF-7 cells, in vitro and are generally not reversed by estradiol or having intrinsic estrogenicity (except the hydroxyphenyl derivative Compound 30). In general the cyclopropane compounds have the formula:

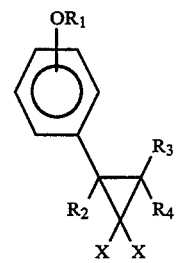

or any pharmaceutically acceptable salt thereof. X is selected from a group consisting of hydrogen and halogen atoms. The group $R_1$ may be a hydrogen atom, an alkyl group, an acyl group, or an arylalkyl group. The group $R_2$ may be a hydrogen atom, an unsubstituted aryl group or a substituted aryl group. The group $R_3$ may be a hydrogen atom, an alkyl group, a cycloalkyl group, a substituted aryl group or an unsubstituted aryl group. The group $R_4$ may be a hydrogen atom, an unsubstituted aryl group or a substituted aryl group. The $R_4$ is absent when $R_3$ is a cycloalkyl group having a first position carbon and a terminal position carbon bonded to the same carbon of the cyclopropane. Further, no more than any two of $R_2$, $R_3$ and $R_4$ has an aryl group.

6 Claims, 9 Drawing Sheets

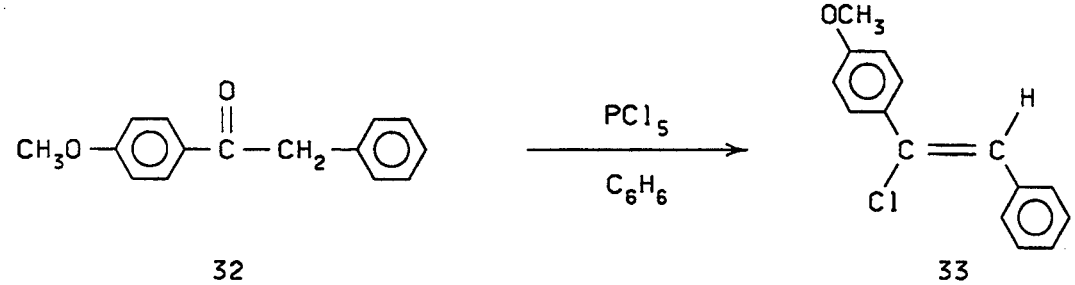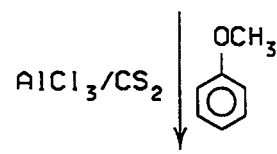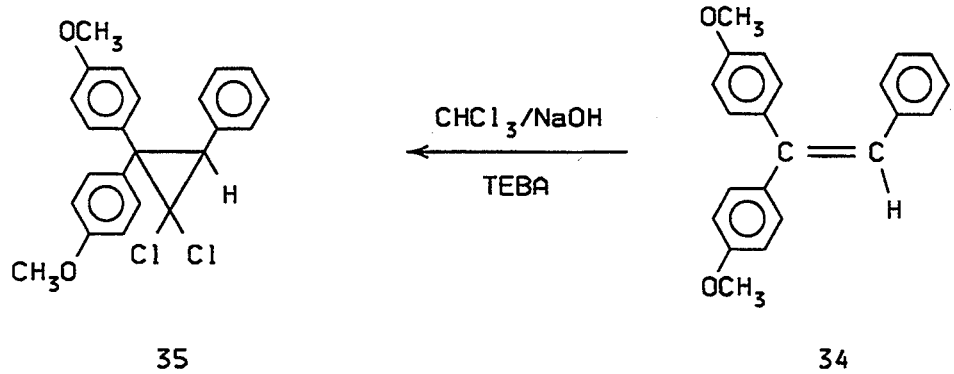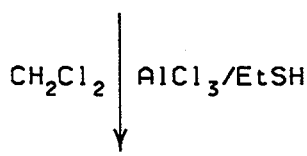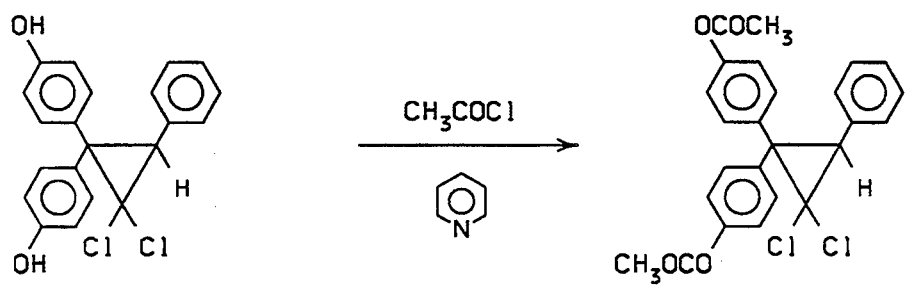
FIG. 4

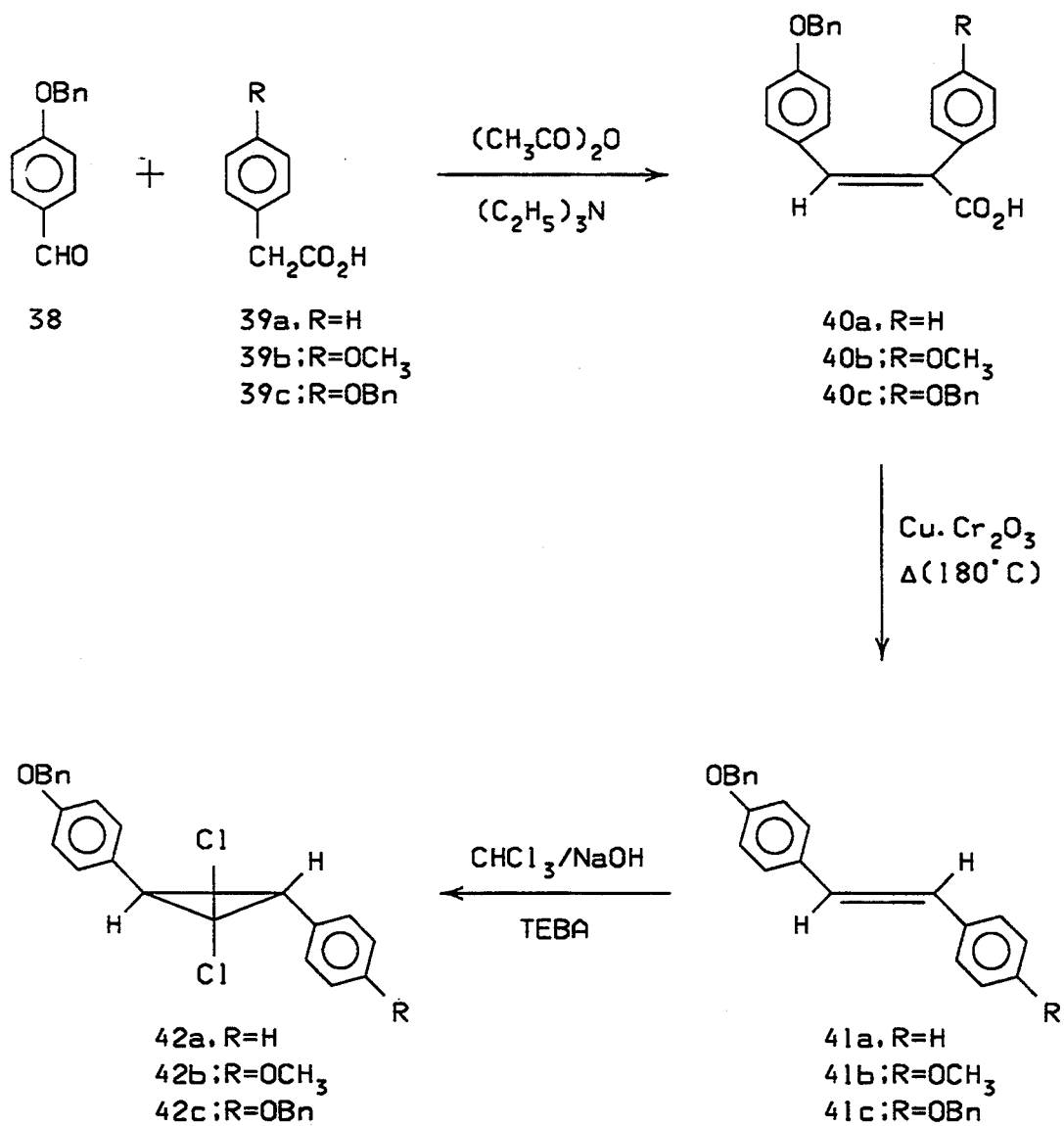
Bn=Benzyl Group
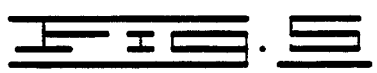

Bn=Benzyl Group

Bn=Benzyl Group

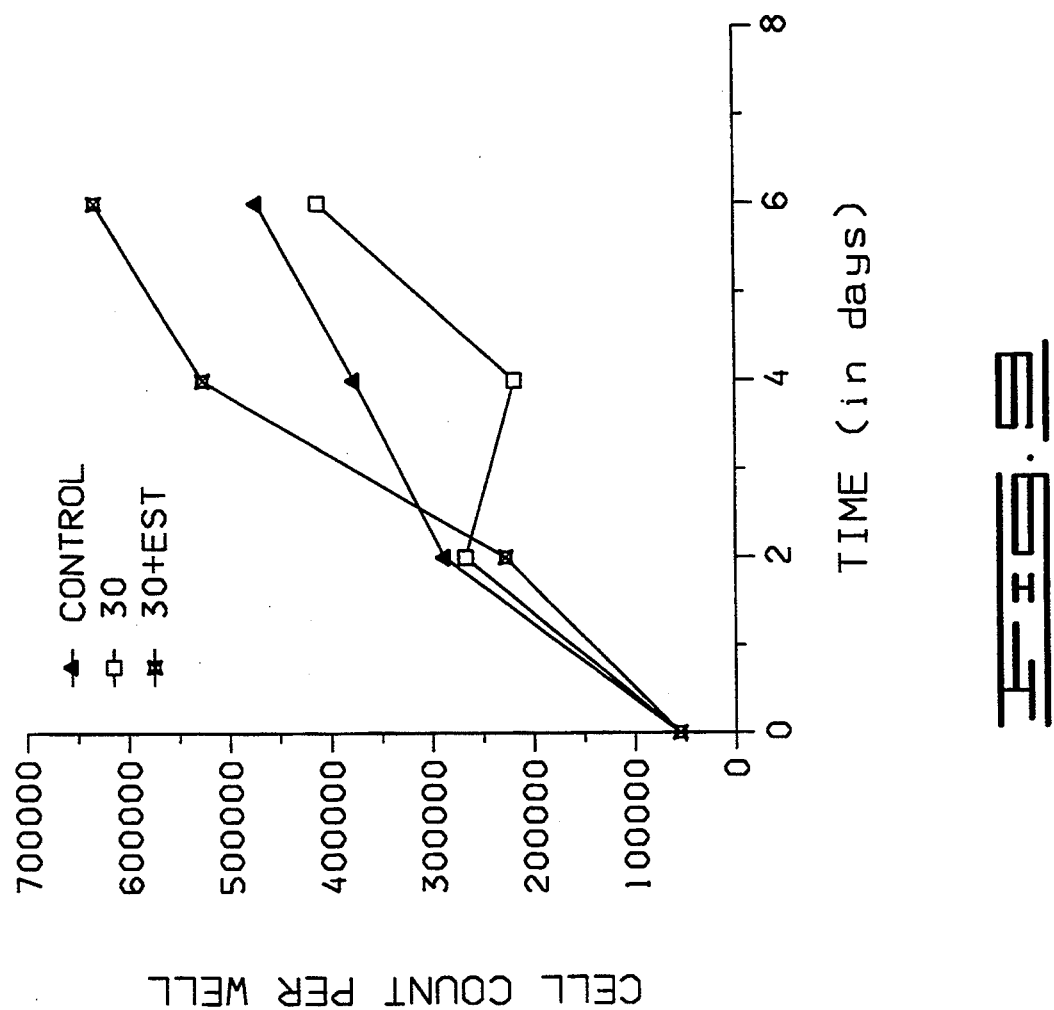

GEM-DICHLOROCYCLOPROPANES AS ANTITUMOR AGENTS

GOVERNMENTAL SUPPORT FOR INVENTION

This invention was made with Government support under a grant from the National Institutes of Health (CA 40458). The Government has certain rights in this invention.

CROSS-REFERENCE TO RELATED APPLICATIONS

This application is a continuation-in-part of Ser. No. 07/812,246, filed Dec. 29, 1991, now abandoned entitled "DIPHENYLCYCLOPROPYL ANALOGS AS ANTIESTROGENIC AND ANTITUMOR AGENTS", which is a continuation-in-part of Ser. No. 07/432,564, filed Nov. 6, 1989, now U.S. Pat. No. 5,098,903, which is a continuation-in-part of Ser. No. 07/098,945, filed Sep. 21, 1987, now U.S. Pat. No. 4,879,315, which is a continuation-in-part of Ser. No. 06/363/429, filed Mar. 30, 1982, now abandoned, which is a continuation-in-part of Ser. No. 06/166,255, filed Jul. 7, 1980, now abandoned, which is a continuation-in-part of Ser. No. 06/128,040, filed Mar. 7, 1980, now abandoned.

BACKGROUND

This invention relates to dichlorocyclopropane compounds and more particularly, but not by way of limitation, to their use as antitumor agents in mammals.

SUMMARY

The present invention comprises Gem-Dichlorocyclopropanes (Analog II derivatives) which demonstrate antiproliferative activity toward MCF-7 cells, in vitro and are generally not reversed by estradiol or having intrinsic estrogenicity. In general the cyclopropane compounds have the formula:

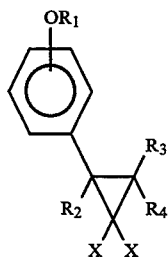

or any pharmaceutically acceptable salts thereof. X is selected from a group consisting of hydrogen and halogen atoms. The group $R_1$ may be a hydrogen atom, an alkyl group, an acyl group, or an arylalkyl group. The group $R_2$ may be a hydrogen atom, an unsubstituted aryl group or a substituted aryl group. The group $R_3$ may be a hydrogen atom, an alkyl group, a substituted aryl group or an unsubstituted aryl group. The group $R_4$ may be a hydrogen atom, an unsubstituted aryl group or a substituted aryl group. The $R_4$ is absent when $R_3$ is a cycloalkyl group having a first position carbon and a terminal position carbon bonded to the same carbon of the cyclopropane. Further, no more than any two of $R_2$, $R_3$ and $R_4$ has an aryl group.

The compounds of the present invention may be combined with a pharmaceutically acceptable carrier to form pharmaceutical compositions. The present invention also comprises a method of inhibiting development of an estrogen-dependent tumor in a mammal in need of such therapy comprising administering to the mammal an effective amount of one or more compounds having the above-described formula.

One object of the present invention is to provide antiestrogenic compounds having antitumor effects which do not concurrently possess estrogen activity.

BRIEF DESCRIPTION OF THE DRAWINGS

FIG. 4 is a scheme showing a synthetic pathway and the chemical structures of Compounds 35 and 37.

FIG. 6 is a scheme showing a synthetic pathway and the chemical structure of Compound 49.

FIG. 9 is a graph demonstrating the influence of Compound 30 on the growth of MCF-7 cells in culture and the reversibility of inhibition by estradiol. Each point represents the mean of duplicate determinations at the time indicated.

DESCRIPTION OF THE INVENTION

Figure 1:
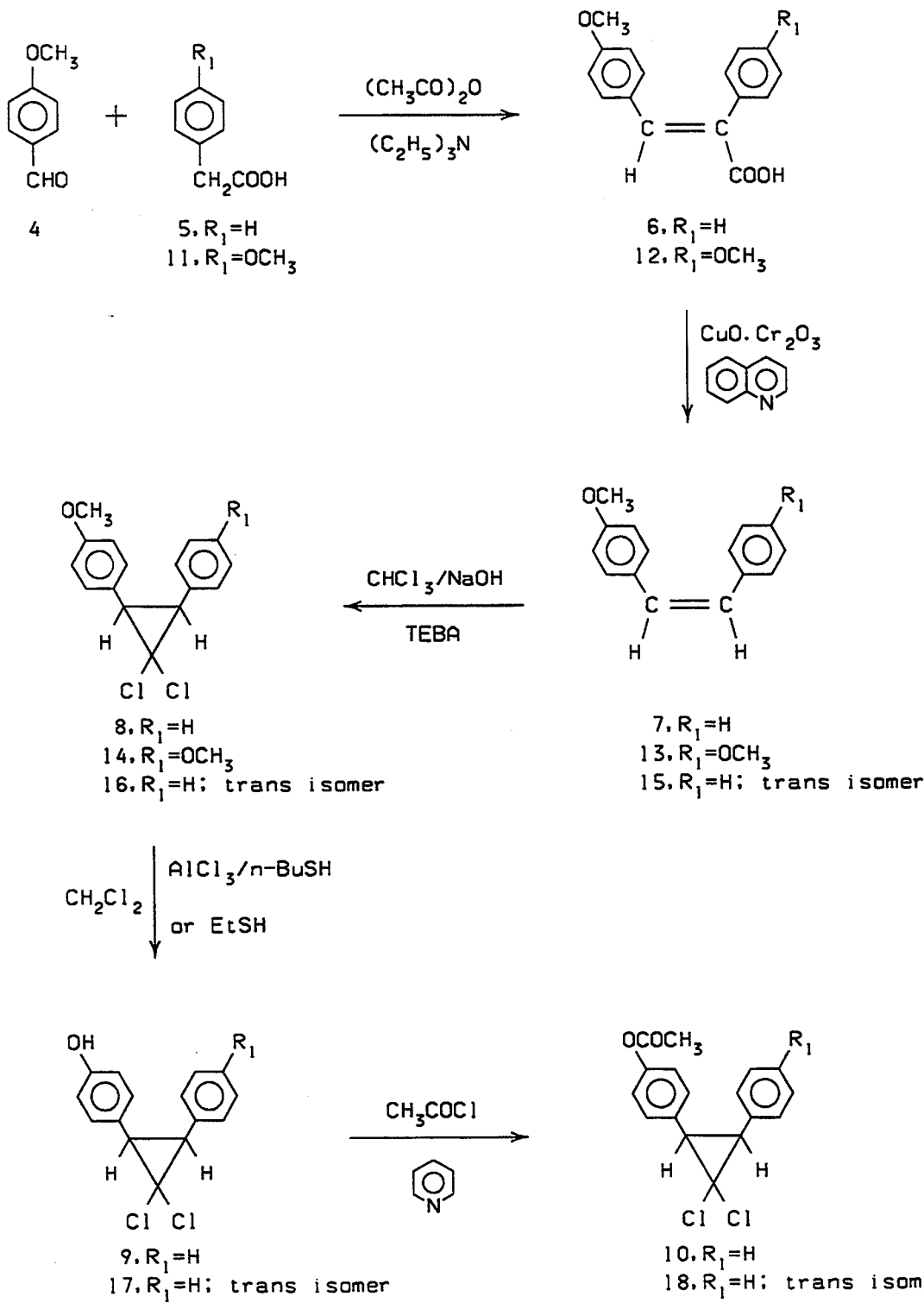
FIG. 1 is a scheme showing a synthetic pathway and the chemical structures of Compounds 8, 10, 14, 16 and 18.
Figure 2:
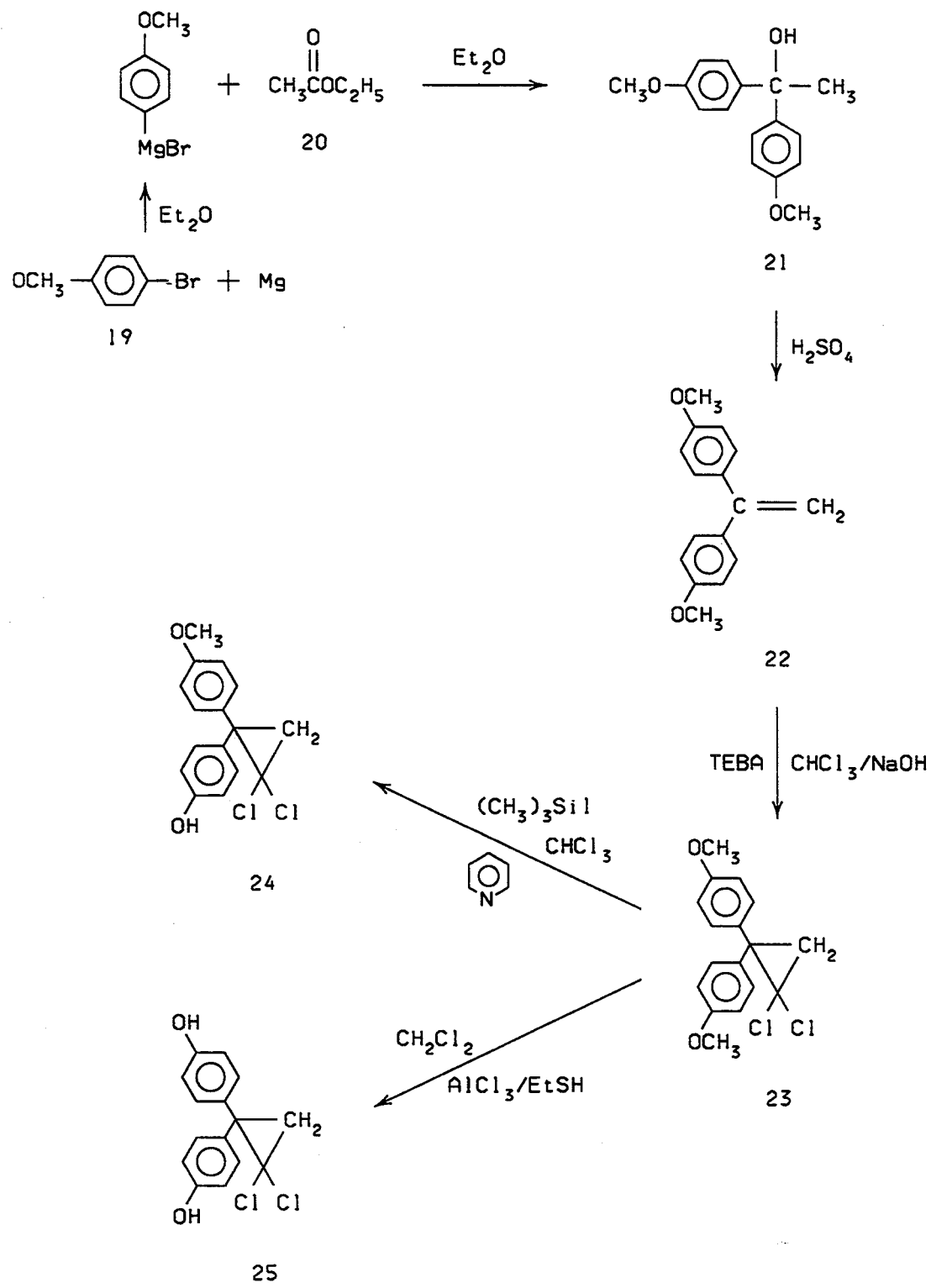
FIG. 2 is a scheme showing a synthetic pathway and the chemical structures of Compounds 23, 24 and 25.
Figure 3:
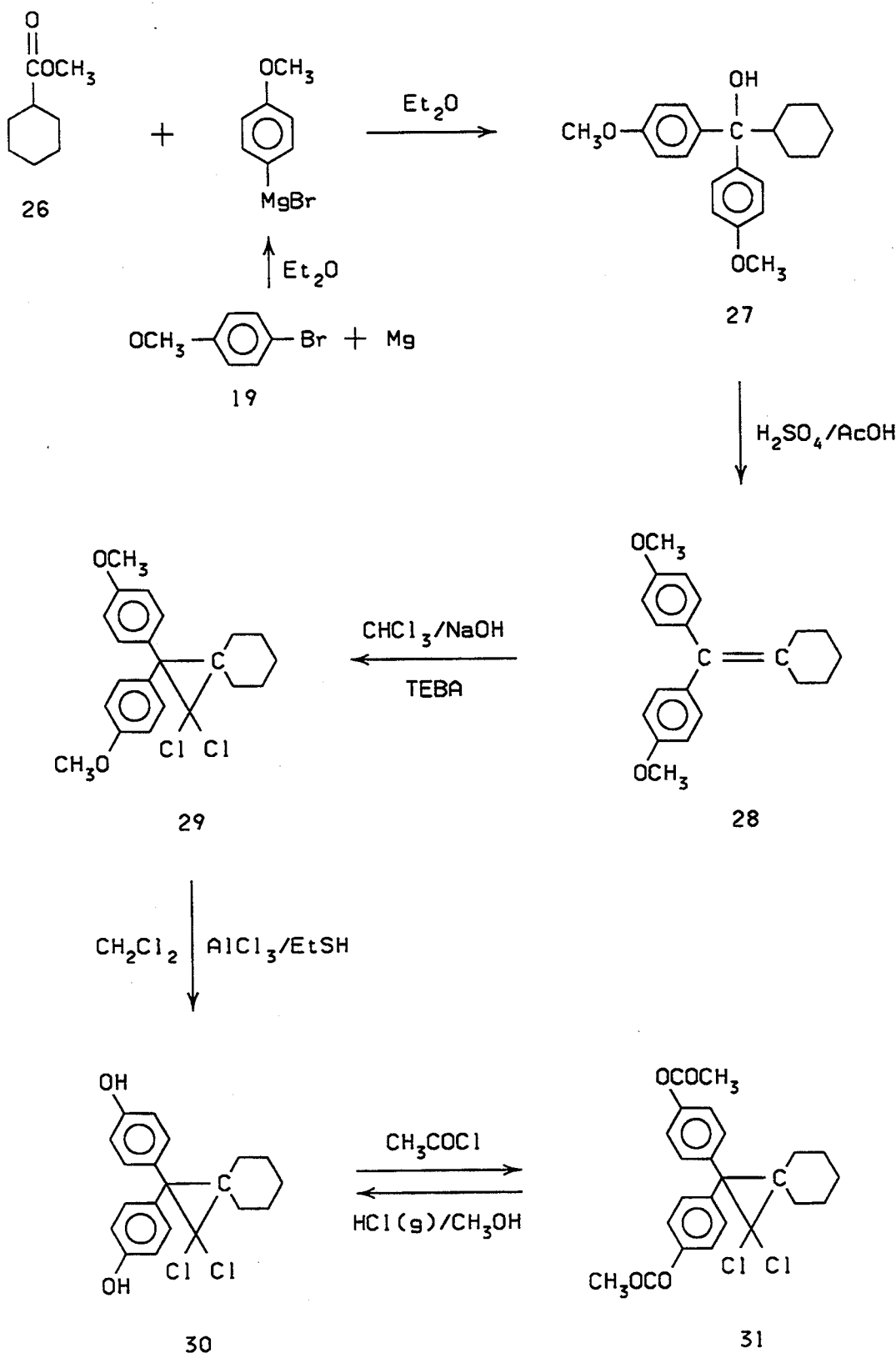
FIG. 3 is a scheme showing a synthetic pathway and the chemical structures of Compounds 29, 30 and 31.

The present invention comprises a compound having the formula:

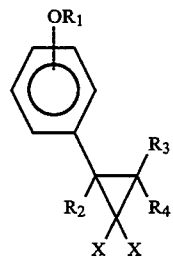

or any pharmaceutically acceptable salt thereof.

X represents a hydrogen or a halogen. Preferably X is a chlorine atom.

$R_1$ represents a hydrogen atom, an alkyl group, an acyl group or an arylalkyl group. Preferably, if $R_1$ is an alkyl group it has from one to four carbons, and more preferably is a methyl group. Preferably if $R_1$ is an acyl group it has from two to four carbons and more preferably is an acetyl group. Preferably if $R_1$ is an arylalkyl group it is a benzyl group.

$R_2$ represents a hydrogen atom or an unsubstituted or a substituted aryl group. Preferably, the unsubstituted aryl group is a phenyl group and the substituent of the substituted aryl group is an alkoxy group or arylalkyloxy group, and more preferably the alkoxy group is a hydroxy group, a methoxy group or an acetoxy group and the arylalkyloxy group is a benzyloxy group.

$R_3$ represents a hydrogen atom, an alkyl group, or a substituted or unsubstituted aryl group. Preferably the unsubstituted aryl group is a phenyl group and the substituted aryl group is a substituted phenyl group. When the substituted aryl group is a substituted phenyl group the substituent is preferably an alkoxy group and more preferably a methoxy group. When $R_3$ is a cycloalkyl group the cycloalkyl group is preferably a cyclopentyl group wherein the first and fifth carbons of the cyclopentyl group are both bonded to the same carbon of the cyclopropane.

$R_4$ represents a hydrogen atom, an unsubstituted or substituted aryl group, or is absent when $R_3$ is a cyclopentyl group. Preferably, when $R_4$ is an unsubstituted aryl group, it is a phenyl group, and when $R_4$ is a substituted aryl group the substituent is an alkoxy or arylalkyloxy group. More preferably when the substituent is an alkoxy group it is a methoxy group and when it is an arylalkyloxy group it is a benzyloxy group. When $R_3$ is a cycloalkyl group having a first position carbon and a terminal position carbon bonded to the same carbon of the cyclopropane, the $R_4$ is absent. No more than any two of $R_2$, $R_3$, and $R_4$ has an aryl group simultaneously. Where $R_1$, $R_2$, $R_3$ or $R_4$ contains or is attached to a phenyl group, any substituted group may be at any position on the respective phenyl group; however the para positions are preferred.

One preferred compound of the present invention comprises 1,1-Dichloro-cis-2-(p-methoxyphenyl)-3-phenylcyclopropane (Compound 8):

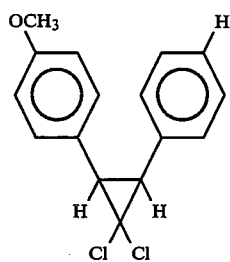

Another preferred compound of the present invention comprises 1,1-Dichloro-cis-2-(p-acetoxyphenyl)-3-phenylcyclopropane (Compound 10):

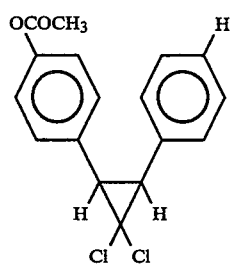

Another preferred compound of the present invention comprises 1,1-Dichloro-cis-2,3-bis-(p-methoxyphenyl)cyclopropane (Compound 14):

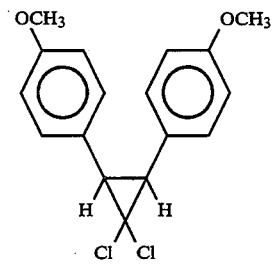

Another preferred compound of the present invention comprises 1,1-Dichloro-trans-2-(p-methoxyphenyl)-3-phenylcyclopropane (Compound 16):

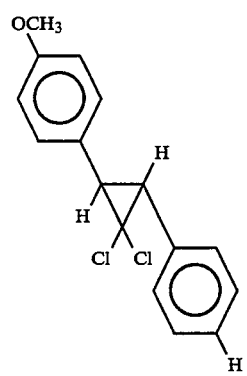

Another preferred compound of the present invention comprises 1,1-Dichloro-trans-2-(p-acetoxyphenyl)-3-phenylcyclopropane (Compound 18):

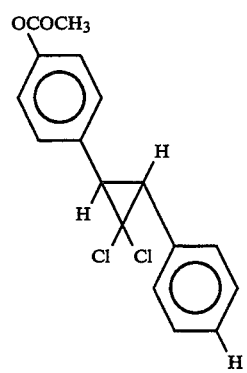

Another preferred compound of the present invention comprises 1,1-Dichloro-2,2-bis-(p-methoxyphenyl)cyclopropane (Compound 23):

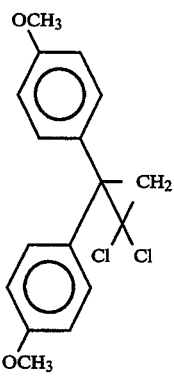

Another preferred compound of the present invention comprises 1,1-Dichloro-2-(p-methoxyphenyl)-2-(p-hydroxyphenyl)cyclopropane (Compound 24):

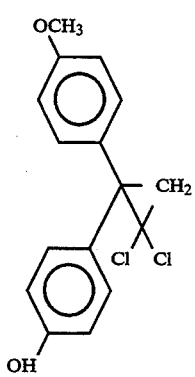

Another preferred compound of the present invention comprises 1,1-Dichloro-2,2-bis-(p-hydroxyphenyl)-cyclopropane (Compound 25):

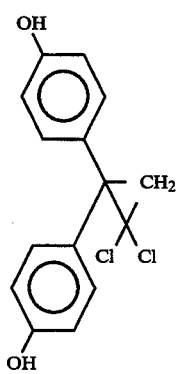

Another preferred compound of the present invention comprises 1,1-Dichloro-2,2-bis-(p-methoxyphenyl)-spiro[2.5]octane (Compound 29):

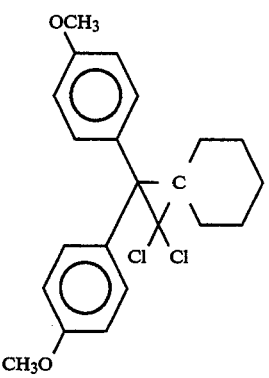

Another preferred compound of the present invention comprises 1,1-Dichloro-2,2-bis-(p-hydroxyphenyl)-spiro[2.5]octane (Compound 30):

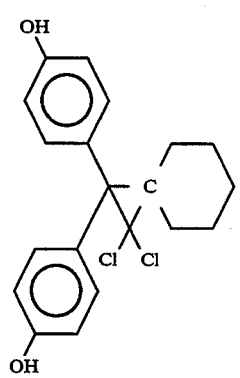

Another preferred compound of the present invention comprises 1,1-Dichloro-2,2-bis-(p-acetoxyphenyl)-spiro[2.5]octane (Compound 31):

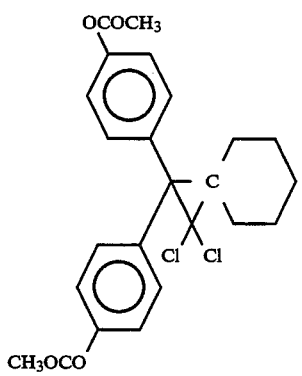

Another preferred compound of the present invention comprises 1,1-Dichloro-2,2-bis-(p-methoxyphenyl)-3-phenylcyclopropane (Compound 35):

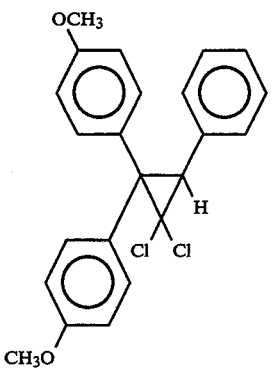

Another preferred compound of the present invention comprises 1,1-Dichloro-2,2-bis-(p-acetoxyphenyl)-3-phenylcyclopropane (Compound 37):

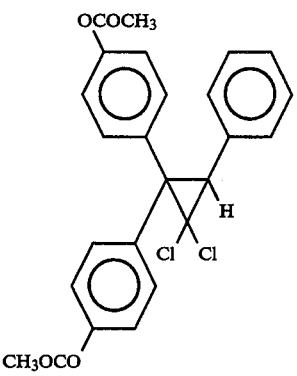

Another preferred compound of the present invention comprises 1,1-Dichloro-trans-2-(p-benzyloxyphenyl)-3-phenylcyclopropane (Compound 42a):

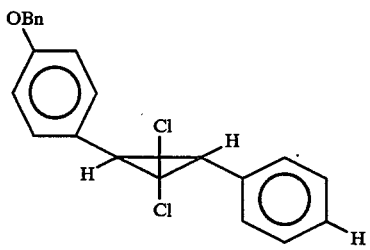

Another preferred compound of the present invention comprises 1,1-Dichloro-trans-2-(p-benzyloxyphenyl)-3-(p-methoxyphenyl)cyclopropane (Compound 42b):

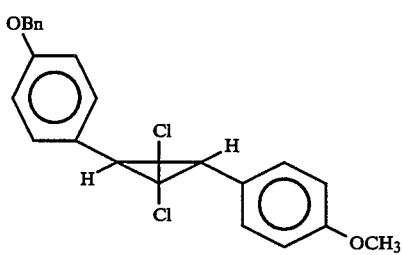

Another preferred compound of the present invention comprises 1,1-Dichloro-trans-2-(p-benzyloxyphenyl)-3-(p-benzyloxyphenyl)cyclopropane (Compound 42c):

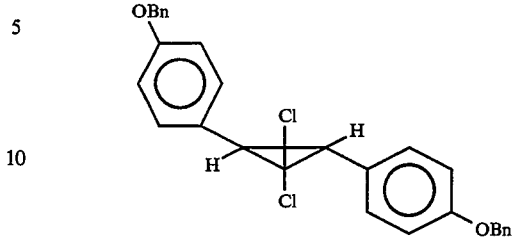

Another preferred compound of the present invention comprises 1,1-Dichloro-2,2-bis-(p-benzyloxyphenyl)-cyclopropane (Compound 49):

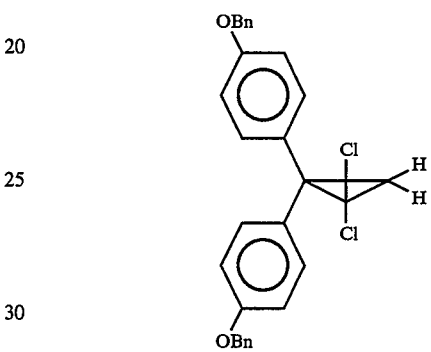

Another preferred compound of the present invention comprises 1,1-Dichloro-2,2-bis(p-benzyloxyphenyl)-spiro[2.5]octane (Compound 53):

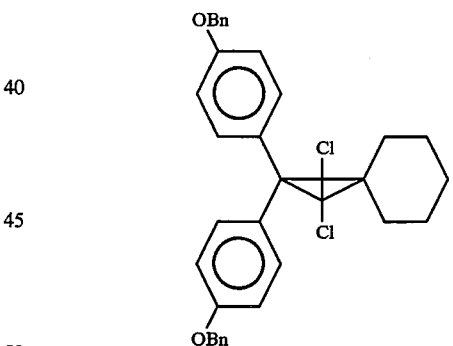

In Compounds 42a, 42b, 42c, 49 and 53 the term "Bn" means a phenyl group.

Preferably, the compounds of the present invention or their salts are combined with a quantity of a pharmaceutically acceptable carrier to form a pharmaceutical composition appropriate for therapeutic delivery to a mammal. The pharmaceutically acceptable carrier should not substantially interfere with the anti-tumor activities of the compound, and may be a solid or liquid in which the compound is solubilized, suspended or dispersed in any manner.

The compounds of the present invention may be administered orally in solid dosage forms, such as tablets and powders, or in liquid dosage forms, such as elixirs, syrups and suspensions; they may also be administered parenterally, in sterile liquid dosage forms. Such parenteral administration may include intravenous, intramuscular, subcutaneous, intra-arterial, and direct tumor perfusion techniques.

If the compound is to be injected, the pharmaceutical carrier should preferably be isotonic, and have about a physiological pH. Suitable pharmaceutical carriers for parenteral administration may be any suitable oil, saline, aqueous dextrose or related sugar solutions, or glycols such as propylene glycol or polyethylene glycols. Solutions for parenteral administration contain preferably a water soluble salt of the active ingredient, suitable stabilizing agents, and if necessary, buffer substances. Additionally, parenteral solutions can contain preservatives. Other suitable pharmaceutical carriers are described in Remington's Pharmaceutical Sciences, Mack Publishing Co., and similar reference texts.

The present invention also comprises a method of inhibiting the development of an estrogen-dependent tumor in a mammal, such as a human, in need of such therapy comprising administering to the mammal a therapeutically effective amount of one or more compounds having the formula described above, preferably in the form of a pharmaceutical composition comprising at least one of the compounds combined with a pharmaceutically acceptable carrier. "Inhibiting the development of an estrogen-dependent tumor" means either slowing the growth of a tumor, diminishing the size of a tumor, or preventing the formation of a tumor from cells having the potential of developing into a tumor wherein the tumor requires the presence of an estrogenic substance for the growth, development and/or metastatic involvement of the tumor.

The compounds previously described may be administered to the mammal to inhibit the development of the estrogen-dependent tumor by an administration method of the type previously described. The dosage may vary according to the type of the disease; the size of the tumor or tumors, if present; and the quantity of tumors as well as the age, weight and health of the recipient; the severity of the condition or disease in the mammal; the kind of concurrent treatment, if any, being administered to the mammal; and the frequency of treatment. Generally, a daily dosage of less than about 0.5 mg to about 2 mg/kg of body weight of the mammal will suffice. The method of administration of the compound of the present invention can be by any suitable method as previously described.

The following examples illustrate the practice of the present invention.

EXAMPLE 1

Preparation of 1,1-Dichloro-cis-2-(p-methoxyphenyl)-3-phenylcyclopropane (Compound 8)

A chilled 29% solution of NaOH (84 g) was added dropwise to a solution of cis-p-methoxystilbene (Compound 7) (7.35 g, 0.035 mol) and triethylbenzylammonium chloride (TEBA) (0.80 g, 0.0035 mol) in 112 mL of $CHCl_3$ with rapid stirring for 16 h. The aqueous layer was extracted with $CH_2Cl_2$. The combined organic layers were washed with saturated NaCl solution and dried over anhydrous $MgSO_4$, filtered, and concentrated to yield a dark-brown oil, which was heated with petroleum ether (bp 30°–60° C.) and filtered to remove the insoluble residue. A light-yellow solid precipitated, and was crystallized in hot petroleum ether. Recrystallization gave white crystals (7.30 g, 71%, mp 59°–60° C.).

$^1H$ NMR ($CDCl_3$) δ 3.25 (s, 2H, ArCH), 3.76 (s, 3H, $OCH_3$), 7.05 (m, 9H, ArH).

EXAMPLE 2

Preparation of 1,1-Dichloro-cis-2-(p-acetoxyphenyl)-3-phenylcyclopropane (Compound 10)

A 10 mL solution of 1,1-dichloro-cis-2-(p-hydroxyphenyl)-3-phenylcyclopropane (Compound 9) (0.009 mol) and pyridine (0.79 g, 0.01 mol) in $Et_2O$ was heated under nitrogen to a gentle reflux, while acetyl chloride (0.78 g, 0.01 mol) was added dropwise slowly via a cannula. A white precipitate was noted immediately, and the mixture was refluxed for 1 h. The reaction flask was cooled while 5 mL of water was added dropwise. $Et_2O$ was used to extract the aqueous layer, and the combined $Et_2O$ layers were washed with 5% $H_2SO_4$, followed b a saturated $NaHCO_3$ solution. Drying with anhydrous $Na_2SO_4$, and evaporation of ether gave a dark-yellow oil, which was chromatographed on a silica gel column and eluted with (3:1) $CH_2Cl_2$/petroleum ether to provide a light-yellow oil (0.9 g, 31%). $^1H$ NMR ($CDCl_3$) δ 2.28 (s, 3H, $OCOCH_3$), 3.30 (s, 2H, ArCH), 7.04 (s, 5H, ArH), 7.28 (m, 4H, ArH).

EXAMPLE 3

Preparation of 1,1-Dichloro-trans-2-(p-methoxyphenyl)-3-phenylcyclopropane (Compound 16)

The phase transfer reaction of trans-p-methoxystilbene (Compound 15) (6.30 g, 0.03 mol) yielded colorless needles (7.37 g, 84%), mp 52.5°–53.5° C. $^1H$ NMR ($CDCl_3$) δ 3.20 (s, 2H, ArCH), 3.83 (s, 3H, $OCH_3$), 7.13 (dd, 4H, substituted ArH), 7.43 (s, 5H, unsubstituted ArH).

EXAMPLE 4

Preparation of 1,1-Dichloro-trans-2-(p-acetoxyphenyl)-3-phenylcyclopropane (Compound 18)

The reaction of 1,1-dichloro-trans-2-(p-hydroxyphenyl)-3-phenylcyclopropane (Compound 17) (0.005 mol) and 0.4 mL of acetyl chloride yielded off-white needles (0.37 g, 22%) from EtOH, mp 124.5°–125.5° C. $^1H$ NMR ($CDCl_3$) δ 2.32 (s, 3H, $OCOCH_3$), 3.20 (s, 2H, ArCH), 6.80–7.58 (m, 9H, ArH).

EXAMPLE 5

Preparation of Bis-(p-methoxy)-cis-stilbene (Compound 13)

The procedure by Greene, (GREENE, F. D., ADAM, W. AND CANTRILL, J. E. (1961), "Diacyl peroxide-olefin reactions. Evidence for a direct reaction", Journal of the American Chemical Society, 83, 3461), was followed. Recrystallization of the decarboxylated 2,3-bis-(p-methoxyphenyl) acrylic acid from petroleum ether gave a solid (58%) with mp 35°–36° C. (lit (Greene et al., 1961) 35.5°–36° C.). $^1H$ NMR ($CDCl_3$) δ 3.80 (s, 6H, $OCH_3$), 6.75 (s, 2H, C=CH), 7.00 (dd, 8H, ArH).

EXAMPLE 6

Preparation of 1,1-Dichloro-cis-2,3-bis-(p-methoxyphenyl)cyclopropane (Compound 14)

The phase transfer reaction of Compound 13 afforded light-yellow fine needles (64%), mp 94.5°–95.5° C. $^1$H NMR (CDCl$_3$) δ 3.23 (s, 2H, ArCH), 3.83 (s, 6H, OCH$_3$), 6.93 (dd, 8H, ArH).

EXAMPLE 7

Preparation of 1,1-Bis-(p-methoxyphenyl)ethylene (Compound 22)

The Grignard reaction of p-bromoanisole (18.7 g, 0.10 mol) and ethyl acetate (3.97 g, 0.045 mol) gave Compound 22 as a light-yellow solid which recrystallized from ethanol gave 4.0 g (37%) of a white flaky solid, mp 140°–141° C. Recrystallization gave a mp of 140.5°–141.5° C., (MIQUEL, J -F., WAHLSTAM, H., OLSSON, K. AND SUNDBECK, B. (1963), "Synthesis of unsymmetrical diphenylalkenes", Journal of Medicinal Chemistry, 6, 774), 142°–143° C. $^1$H NMR (CDCl$_3$) δ 3.83 (s, 6H, OCH$_3$), 5.30 (s, 2H, C=CH$_2$), 7.13 (dd, 8H, ArH).

EXAMPLE 8

Preparation of 1,1-Dichloro-2,2-bis-(p-methoxyphenyl)cyclopropane (Compound 23)

The phase transfer reaction of Compound 22 (4.80 g, 0.020 mol) gave 4.66 g (72%) of yellow needles from cyclohexane/EtOH (40/50), mp 137.5°–138° C. $^1$H NMR (CDCl$_3$) δ 2.20 (s, 2H, CH$_2$), 3.83 (s, 6H, OCH$_3$), 7.10 (dd, 8H, ArH).

EXAMPLE 9

Preparation of 1,1-Dichloro-2-(p-methoxyphenyl)-2-(p-hydroxyphenyl)cyclopropane (Compound 24), and 1,1-Dichloro-2,2-bis-(p-hydroxyphenyl)cyclopropane (Compound 25)

Method A. The demethylation of Compound 23 followed the procedure of Jung (JUNG, M. E. AND LYSTER, M. A. (1977), "Quantitative dealkylation of alkyl ethers via treatment with trimethylsilyl iodide. A new method for ether hydrolysis", Journal of Organic Chemistry, 42, 3761; JUNG, M. E. AND LYSTER, M. A. (1980), "Cleavage of methyl ethers with iodotrimethylsilane: cyclohexanol from cyclohexyl methyl ether", Organic Syntheses, 59, 35), using iodotrimethylsilane, pyridine and chloroform. A yellow solid was separated by column chromatography using silica gel and eluted with CH$_2$Cl$_2$/(CH$_3$)$_2$CO (95:5). Compound 24 was recrystallized in hexane with a trace of ethanol to give fine colorless needles, mp 153°–155° C. (dec). $^1$H NMR (CDCl$_3$) δ 2.23 (s, 2H, CH$_2$), 3.80 (s, 6H, OCH$_3$), 6.83–7.53 (2dd, 8H, ArH). Compound 25 was eluted from the column with acetone to give a reddish brown solid. Recrystallization in CHCl$_3$ gave a light-pink solid, mp 185°–192° C. (dec).

Method B. The demethylation of Compound 23 followed the method of Node (NODE, M., NISHIDE, K., FUJI, K. AND FUJITA, E. (1980), "Hard acid and soft nucleophile system. 2. demethylation of methyl ethers of alcohol and phenol with an aluminum halide-thiol system", Journal of Organic Chemistry, 45, 4275), using n-BuSH and AlCl$_3$. The crude product was separated by column chromatography on silica gel to yield both Compounds 24 and 25. Compound 24 was obtained by collecting the fractions eluted with CH$_2$Cl$_2$/petroleum ether/EtOAc (70/20/10). Recrystallization in CHCl$_3$ gave Compound 24 (58.9%) as colorless fine needles, mp 154°–155° C. (dec). The fractions eluted with CH$_2$Cl$_2$/EtOAc (90:10 and 80:20) were collected to afford Compound 25. Recrystallization of Compound 25 in CHCl$_3$ gave colorless fine needles (55.3%), mp 188°–189° C. (dec) which was dried for one week. $^1$H NMR (CDCl$_3$/d$_6$-DMSO) δ 2.26 (s, 2H, CH$_2$), 7.13 (dd, 8H, ArH), 8.38 (s, 2H, OH).

EXAMPLE 10

Preparation of Bis-(p-methoxyphenyl)-cyclohexylidene methane (Compound 28)

The Grignard reaction of p-bromoanisole (15.0 g, 0.080 mol) and methyl cyclohexane carboxylate (Compound 26) (5.7 g, 0.040 mol) afforded the carbinol (Compound 27) which upon dehydration yielded a yellow solid. Recrystallized from absolute EtOH yielded 8.0 g (65%) of a colorless solid, mp 106°–107° C. (MIQUEL, J -F., WAHLSTAM, H., OLSSON, K. AND SUNDBECK, B. (1963), "Synthesis of unsymmetrical diphenylalkenes", Journal of Medicinal Chemistry, 6, 774), 109°–110° C. $^1$H NMR (CDCl$_3$) δ 1.70 (broad s, 10H, cyclohexyl), 3.70 (s, 6H, OCH$_3$), 7.07 (dd, 8H, ArH).

EXAMPLE 11

Preparation of 1,1-Dichloro-2,2-bis-(p-methoxyphenyl)-spiro[2.5]octane (Compound 29)

A phase transfer reaction of Compound 28 (6.16 g, 0.020 mol) gave a dark-brown, thick oil, which was warmed with 50 mL of petroleum ether (bp 30°–60° C.). The insoluble residue was filtered, and a yellow solid precipitated from the petroleum ether filtrate. Light-yellow needles were obtained from subsequent recrystallizations in cyclohexane (1.9 g, 24%), mp 121°–121.5° C. $^1$H NMR (CDCl$_3$) δ 1.70 (broad s, 10H, cyclohexyl), 3.70 (s, 6H, OCH$_3$), 7.07 (dd, 8H, ArH).

EXAMPLE 12

Preparation of 1,1-Dichloro-2,2-bis-(p-hydroxyphenyl)-spiro[2.5]octane (Compound 30)

The demethylation of Compound 29 followed the method of Node (Node et al., 1980). The crude product was recrystallized in CH$_2$Cl$_2$, and subsequent recrystallizations in CH$_2$Cl$_2$ with a few drops of absolute EtOH gave 0.78 g small colorless needles (54%), mp 136.5°–137.5° C. (dec.), and gradually turned to light-orange. Compound 30 also was obtained and thus confirmed via the di-acetate Compound 31 (1,1-Dichloro-2,2-bis-(p-acetoxyphenyl)-spiro[2.5]octane) by the following method: The di-acetate Compound 31 (0.46 g, 0.001 mol) in 35 mL CH$_3$OH was heated for 15 min., while 10 mL of CH$_2$Cl$_2$ was added to give a clear colorless solution. A stream of dry HCl(g) was bubbled through the solution for 2 min (the flask was rotated to ensure complete saturation of HCl). The solvent was evaporated in vacuo to give a purple mass which was recrystallized from CH$_2$Cl$_2$ with a few drops of absolute EtOH to yield fine colorless needles, mp 137°–137.5° C. (dec). Subsequent crystallization from the mother liquor gave a total 0.25 g of 30 in 67% yield. $^1$H NMR (CDCl$_3$/d$_6$-DMSO) δ 1.68 (broad s, 10H, cyclohexyl), 6.83 (dd, 8H, ArH), 8.50 (s, 2H, ArOH).

EXAMPLE 13

Preparation of 1,1-Dichloro-2,2-bis-(p-acetoxyphenyl)-spiro[2.5]octane (Compound 31)

Compound 30 (0.58 g, 0.0016 mol) was acetylated with 0.8 mL of pyridine and 0.8 mL of acetyl chloride. Recrystallization from absolute EtOH yielded 0.46 g (64%) light-yellow needles, mp 162°–163° C. $^1$H NMR (CDCl$_3$) δ 1.70 (broad s, 10H, cyclohexyl), 2.25 (s, 6H, OCOCH$_3$), 7.21 (dd, 8H, ArH).

EXAMPLE 14

Preparation of p-Methoxy-α-chlorostilbene (Compound 33)

The procedure of Nagano (NAGANO. T. (1955), "Triphenylethylene derivatives", Journal of the American Chemical Society, 77, 1691), was followed wherein p-methoxydeoxybenzoin (Compound 32) is treated with PCl$_5$ in refluxing benzene. A reddish oil, obtained upon evaporation of the solvent in vacuo and solidified immediately, was recrystallized from EtOH to give colorless plates (80%), mp 70°–71° C. (lit (Nagano, 1955) 72°–72° C.). $^1$H NMR (CDCL$_3$) δ 3.83 (s, 3H, (OCH$_3$), 6.86–7.86 (m, 10H, ArH and C=CH).

EXAMPLE 15

Preparation of 1,1-Bis-(p-methoxyphenyl)-2-phenylethylene (Compound 34)

Compound 33 (4.8 g, 0.020 mol) was condensed with anisole (2.6 g, 0.024 mol) in a Friedel-Craft reaction using pulverized AlCl$_3$ (3.4 g, 0.026 mol). The crude orange oil was treated with EtOH to yield 34 as a solid (5.47 g, 78.7% yield), mp 61.5°–62.5° C. (lit (Nagano, 1955) 64°–65° C.). $^1$H NMR (CDCl$_3$) δ 3.83 (s, 6H, OCH$_3$), 6.77–7.37 (dd, 8H, substituted ArH), 6.85 (s, 1H, C=CH), 7.12 (s, 5H, unsubstituted ArH).

EXAMPLE 16

Preparation of 1,1-Dichloro-2,2-bis-(p-methoxyphenyl)-3-phenylcyclopropane (Compound 35)

The phase transfer reaction of Compound 34 (4.74 g, 0.015 mol) gave a crude product which was recrystallized in cyclohexane/ethanol (60:40) to give light-yellow crystals (60%), mp 124°–125° C. $^1$H NMR (CDCl$_3$) δ 3.53 (s, 1H, ArCH), 3.77 (s, 6H, OCH$_3$), 6.73–7.56 (m, 13H, ArH).

EXAMPLE 17

Preparation of 1,1-Dichloro-2,2-bis-(p-acetoxyphenyl)-3-phenylcyclopropane (Compound 37)

Acetylation of Compound 36 (0.6 g, 0.0016 mol) was performed with pyridine (0.8 mL) and acetyl chloride (0.8 mL) as described in the preparation of Compound 10. The crude product was chromatographed (silica gel; CH$_2$Cl$_2$/acetone, 98:2) to provide 0.02 g colorless amorphous solid, mp 74°–75° C. The fractions eluted with CH$_2$Cl$_2$/acetone (95:5) had both the acetate and the phenolic products, which were subjected to acetylation. Additional purification provided a total 0.1 g of Compound 37 (13.7%). $^1$H NMR (CDCl$_3$) δ 2.26 (s, 6H, OCOCH$_3$), 3.55 (s, 1H, ArCH), 6.96–7.66 (m, 13H, ArH).

EXAMPLE 18

Preparation of 1,1-Dichloro-trans-2-(p-benzyloxyphenyl)-3-phenylcyclopropane (Compound 42a), 1,1-Dichloro-trans-2-(p-benzyloxyphenyl)-3-(p-methoxyphenyl)cyclopropane (Compound 42b), and 1,1-Dichloro-trans-2-(p-benzyloxyphenyl)-3-(p-benzyloxyphenyl)cyclopropane (Compound 42c)

Figure 5:
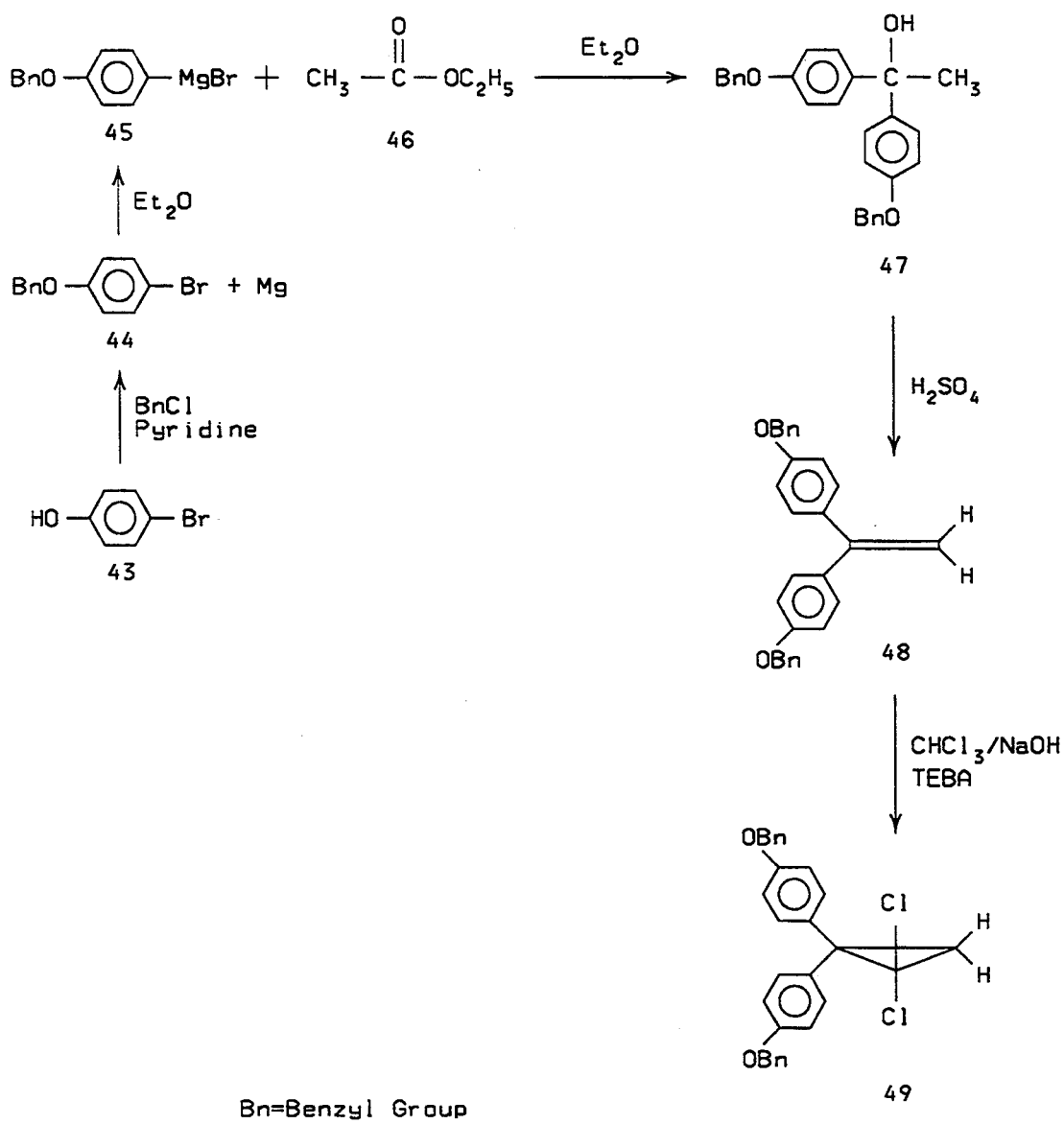
FIG. 5 is a scheme showing a synthetic pathway and the chemical structures of Compounds 42a, 42b and 42c.

The cis-α-phenyl-p-benzyloxycinnamic acid (40a) and derivatives (40b & c) can be prepared (FIG. 5) by the condensation of p-benzyloxybenzaldehyde (38) with phenylacetic acid (39a) and its derivatives (39b & c) in the presence of acetic anhydride and triethylamine. The crude acids (40a–40c) are washed with 20% NaOH followed by acidifying the aqueous layer with HCl. The decarboxylation occurs at 180° with the release of carbon dioxide to yield the stable tran-isomers (41a–c). Ethanol can be used to crystallize the crude reaction mixtures. Concentration of the mother liquor and crystallization of the oils from petroleum ether affords the p-benzyloxy-trans-stilbene derivatives (41a–c); which are allowed to react with a solution of triethylbenzylammonium chloride in chloroform. A cold solution of sodium hydroxide (29%) is added dropwise with stirring. The aqueous layers are extracted with three 50 ml portions CH$_2$Cl$_2$. The organic layers are filtered and evaporated in vacuo, which yield dark brown oils and crystallize from petroleum ether. Recrystallizations are usually performed by dissolving the solid (42a–c) in hot petroleum ether.

EXAMPLE 19

Preparation of 1,1-Dichloro-2,2-bis-(p-benzyloxyphenyl)-cyclopropane (Compound 49)

Para-Benzyloxyphenyl bromide (44) is prepared (FIG. 6) from the reaction of p-bromophenol (43) and benzyl chloride refluxed in pyridine. Compound 44 is subsequently converted to the Grignard reagent 45 when it is allowed to react with magnesium turnings in anhydrous ether. This Grignard reagent is added dropwise to ethyl acetate dissolved in anhydrous ether and allowed to reflux for at least 1 hour, and then cooled at room temperature to form the alcohol (47). The alcohol is not isolated; but remains in solution, to which is added slowly sulfuric acid (5N) while the reaction vessel is cooled in an ice bath and ether is added. After stirring for two hours and remaining at room temperature for 24 hours, the mixture is extracted with chloroform and dried over anhydrous magnesium sulfate, evaporated in vacuo to yield the solid Compound 48. Recrystallization is usually performed in ethanol. A solution of the pure Compound 48 and triethylbenzylammonium chloride in chloroform is treated with 29% cold solution of sodium chloride in a dropwise fashion over two hours. This solution is allowed to continue stirring for 12 hours and then the aqueous layer is extracted with CH$_2$Cl$_2$. The combined methylene chloride layers are filtered and evaporated in vacuo which yields the solid form of Compound 49. Recrystallization is carried out in the appropriate solvent (ethanol or cyclohexane/ethanol).

EXAMPLE 20

Preparation of 1,1-Dichloro-2,2-bis(p-benzyloxyphenyl)-spiro[2.5]octane (Compound 53)

The Grignard reagent 45 is prepared as described earlier (Example 19). To this Grignard reagent is added dropwise methyl cyclohexane carboxylate (5) dissolved in anhydrous ether. After refluxing for at least one hour, the reaction solution is poured over crushed ice to which is added concentrated sulfuric acid/acetic acid (1:3) to dehydrate Compound 51 which was formed in the reaction. The mixture usually solidifies after the acids are added and ether is added to dissolve the solid and the solution is stirred for at least two hours at room temperature. The aqueous layer is then extracted with ether and the combined ether layers are washed with 10% sulfuric acid and dried over anhydrous sodium sulfate.

Figure 7:
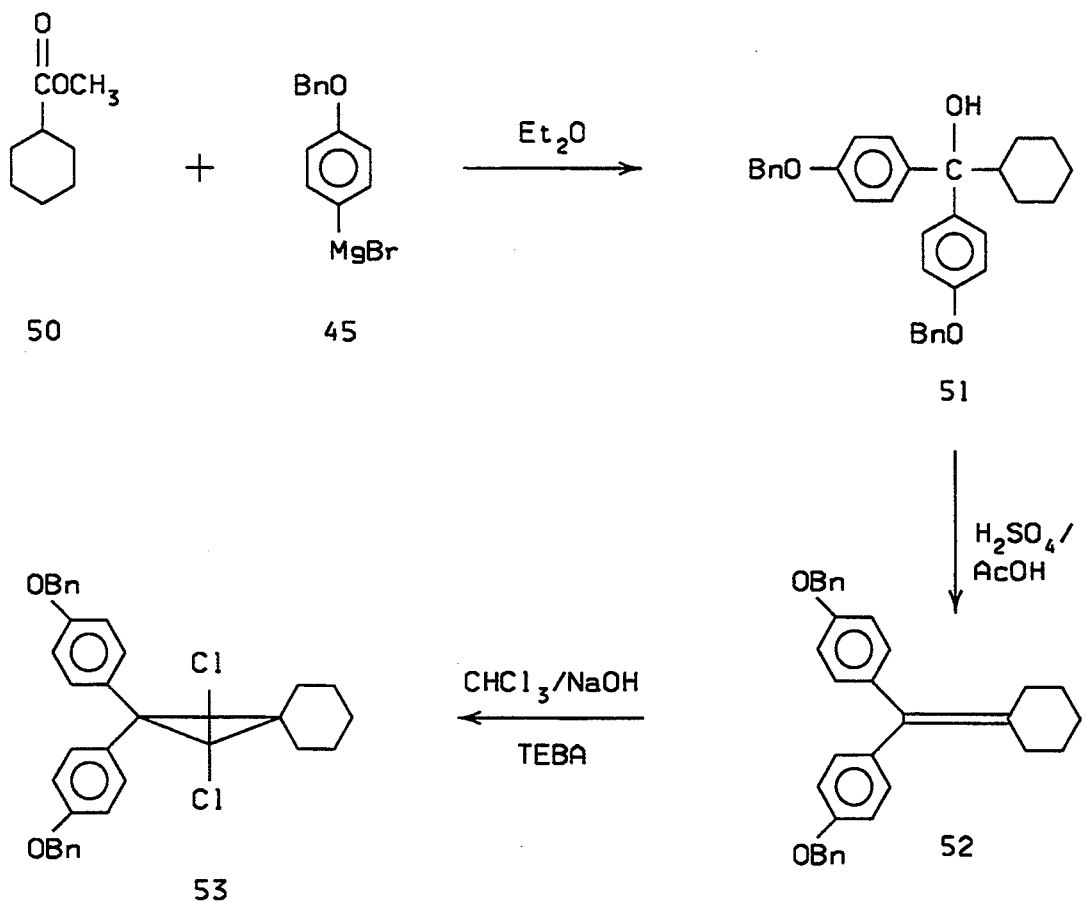
FIG. 7 is a scheme showing a synthetic pathway and the chemical structure of Compound 53.

Upon evaporation of the solvent in vacuo, the solid (52) forms which is recrystallized from ethanol to a solution of Compound 52 and triethylbenzylammonium chloride (TEBA) in chloroform is added in a dropwise manner, a cold solution of 50% sodium hydroxide, and allowed to stir at room temperature for 72 hours. Water is then added and the aqueous layer is extracted with methylene chloride. The combined organic layers are washed with a saturated sodium chloride solution and dried over anhydrous magnesium sulfate. Filtration and concentration in vacuo usually affords a dark oil (crude 53) which is heated in petroleum ether to precipitate the solid (53), which can be recrystallized from cyclohexane to yield pure Compound 53 (FIG. 7).

EXAMPLE 21

Chemistry

The structures of all compounds were supported by their proton NMR spectra, which were measured on either a Varian EM-360A or XL-300 spectrometer. The spectra are reported in parts per million in CDCl$_3$ unless otherwise noted, with tetramethylsilane as the internal standard. Infrared spectra were obtained from KBr pellets on a Beckman Acculab 1 spectrometer and were consistent with the assigned structures. Silica gel (for example, obtained commercially from J. T. Baker) of approximately 40 μm diameter was used for flash chromatography (STILL, W. C., KAHN, M. AND MITRA, A. (1978), "Rapid chromatographic technique for preparative separations with moderate resolutions", Journal of Organic Chemistry, 43, 2923), which was performed at 5–10 psi. Petroleum ether was of bp 30°–60° C. When necessary, solvents or reagents were dried by appropriate methods. Evaporations were carried out in vacuo on a rotary evaporator or under a stream of dry N$_2$. Melting points were taken on a Thomas-Hoover capillary melting point apparatus and are uncorrected. Reaction progress and product purity were monitored by analytical TLC on strips of Eastman Kodak plastic-backed SiO$_2$ 60 F$_{254}$ or Al$_2$O$_3$ F$_{254}$. Developed strips were viewed under light of 254 and 365 nm wavelengths. Elemental analyses were done by Midwest Microlab Ltd., Indianapolis, Ind. Acceptable elemental results are denoted in Table I by the formula, followed by the elements analyzed. Melting points and yields of all compounds were based on pure samples unless otherwise noted, are listed in Table I. Para-Bromoanisole, p-methoxydeoxybenzoin, anisole, p-methoxybenzaldehyde, and 2,3-bis-(p-methoxyphenyl)-acrylic acid and trans-p-methoxystilbene (the olefin), were purchased from Aldrich & Co. The cyclopropanes 1,1-dichloro-cis-2-(p-hydroxyphenyl)-3-phenylcyclopropane (9), and its trans isomer 1,1-dichloro-trans-2-(p-Hydroxyphenyl)-3-phenylcyclopropane 17) were prepared from Compounds 8 & 16, respectively. Compound 9 was not concentrated because of its instability to air and light, and hence remained in solution (monitored by TLC) to prepare the acetate derivative (Compound 10). Tamoxifen was obtained from Stuart Pharmaceuticals, Division of ICI Americas, Inc., Wilmington, Del. 19897. MER 25 was obtained from the Merrell Dow Research Institute, Division of Merrell Dow Pharmaceuticals, Inc., Cincinnati, Ohio. Protein Assay Reagent, Pierce Chemical Co., Rockford, Ill. 61105. Diethylstilbestrol, β-estradiol, EDTA, DL-dithiothreitol, Sodium molybdate, and Tris (hydroxymethyl) aminomethane hydrochloride were purchased from Sigma Chemical Co., St. Louis, Mo. 63178.

The gem-dichlorocyclopropanes synthesized (FIGS. 1–4) are shown in Table I. The general synthetic route to the diarylcyclopropanes is shown in FIG. 1. Standard procedures were followed to prepare cis-α'-phenyl-p-methoxycinnamic acid (Compound 6) as previously described (Buckles & Hausman, 1948; Buckles et al., 1951; Buckles & Bremer, 1953). Recrystallization of the solid from aqueous ethanol (95%) afforded light-yellow needles (54%), mp 188°–189° C. (lit (Buckles et al., 1951) 188°–189° C.). $^1$H NMR (CDCl$_3$) δ 3.80 (s, 3H, OCH$_3$), 6.65–7.50 (m, 9H, ArH), 7.95 (s, 1H, C=CH).

TABLE I

Yields and Physical Characteristics of 1,1-Dichloro-2,2(3)- diaryl and 2,2,3-triarylcyclopropanes.

| No. | R$_1$ | R$_2$ | R$_3$ | R$_4$ | Yield,%$^a$ | mp, °C. | formula |
|---|---|---|---|---|---|---|---|
| 8 | CH$_3$ | H | C$_6$H$_5$ | H | 71 | 59–60$^b$ | C$_{16}$H$_{14}$Cl$_2$O |
| 10 | COCH$_3$ | H | C$_6$H$_5$ | H | 31 | oil | C$_7$H$_{14}$Cl$_2$O |
| 14 | CH$_3$ | H | 4-OCH$_3$—C$_6$H$_4$ | H | 64 | 94.5–95.5$^c$ | C$_{27}$H$_{10}$Cl$_2$O$_2$ |
| 16 | CH$_3$ | H | H | C$_6$H$_5$ | 84 | 52.5–53.5$^b$ | C$_{16}$H$_{14}$Cl$_2$O |
| 18 | COCH$_3$ | H | H | C$_6$H$_5$ | 22 | 124.5–125.5$^d$ | C$_{17}$H$_{14}$Cl$_2$O$_2$ |
| 23 | CH$_3$ | 4-OCH$_3$—C$_6$H$_4$ | H | H | 72 | 137.5–138$^e$ | C$_{17}$H$_{16}$Cl$_2$O$_2$ |
| 21 | CH$_3$ | 4-OH—C$_6$H$_4$ | H | H | 58 | 154–155$^f$ | C$_{16}$H$_{14}$Cl$_2$O$_2$ |
| 25 | H | 4-OH—C$_6$H$_4$ | H | H | 55 | 188–189$^f$ | C$_{15}$H$_{12}$Cl$_2$O$_2$ |
| 29 | CH$_3$ | 4-OCH$_3$—C$_6$H$_4$ | (CH$_2$)$_5$ | — | 24 | 121–121.5$^g$ | C$_{22}$H$_{24}$Cl$_2$O$_2$ |
| 30 | H | 4-OH—C$_6$H$_4$ | (CH$_2$)$_5$ | — | 67$^h$ | 137–137.5$^i$ | C$_{20}$H$_{20}$Cl$_2$O$_2$ |
| 31 | COCH$_3$ | 4-OCOCH$_3$—C$_6$H$_4$ | (CH$_2$)$_5$ | — | 64 | 162–163$^d$ | C$_{24}$H$_{24}$Cl$_2$O$_4$ |
| 35 | CH$_3$ | 4-OCH$_3$—C$_6$H$_4$ | C$_6$H$_5$ | H | 60 | 124–125$^e$ | C$_{23}$H$_{20}$Cl$_2$O$_2$ |

TABLE I-continued
Yields and Physical Characteristics of 1,1-Dichloro-2,2(3)- diaryl and 2,2,3-triarylcyclopropanes.

| No. | $R_1$ | $R_2$ | $R_3$ | $R_4$ | Yield,%[a] | mp, °C. | formula |
|---|---|---|---|---|---|---|---|
| 37 | $COCH_3$ | $4\text{-}OCOCH_3\text{-}C_6H_4$ | $C_6H_5$ | H | 13 | 74–75[j] | $C_{25}H_{20}Cl_2O_4$ |

[a]No attempts were made to optimize yields.
[b]Petroleum ether.
[c]Hexane.
[d]EtOH.
[e]Cyclohexane/EtOH.
[f]Decomposed, $CHCl_3$.
[g]Cyclohexane.
[h]From acidic hydrolysis via 31.
[i]$CH_2Cl_2$/EtOH.
[j]$SiO_2$ chromatography.

Standard procedures of Taylor (Taylor & Crawford, 1934), Kon (Kon & Spickett, 1949) and Buckles (Buckles & Wheeler, 1953) were followed to synthesize cis-p-methoxystilbene (Compound 7). The brown oil was chromatographed on a silica gel column and eluted with petroleum ether/$CH_2Cl_2$ (20:80) yielding cis-p-methoxystilbene 7 (90%). $^1H$ NMR ($CDCl_3$) δ 3.80 (s, 3H, $OCH_3$), 6.55 (s, 2H, 2 C=CH), 6.70–7.30 (m, 9H, ArH). These standard references are hereby incorporated herein by reference.

Essentially, the intermediate olefin acids (Compounds 6 & 12) were obtained from a mixed Perkin and Knoevenagel-type condensation involving the reaction of p-methoxybenzaldehyde (Compound 4) with phenylacetic acid (Compound 5), or p-methoxyphenylacetic acid (Compound 11) in triethylamime and acetic anhydride. To prepare cis-p-methoxystilbene (Compound 7) or bis-(p-methoxy)-cis-stilbene (Compound 13). Decarboxylation of 6 & 12 with quinoline (prevents isomerization; KLEIN, J. AND MEYER, A. Y. (1964), "The decarboxylation of α-cyano-and α-carboxycinnamic acids", Journal of Organic Chemistry, 29, 1038), and copper chromite at elevated temperature provided 7 & 13. High temperature during distillation caused 8% isomerization to the trans-isomer (15), which was isolated by column chromatography. Dichlorocarbene generation used the catalytic phase transfer method (21, 37) (used extensively in our laboratory) of 50% aqueous solution of NaOH, $CHCl_3$ and benzyltriethylammonium chloride (TEBA) as the anion transfer agent. Preparation of the gem-dichlorocyclopropyl compounds (8, 14, 16) from their olefin precursors (7, 13, 15) followed this improved phase-transfer method (MAGARIAN, R. A. AND BENJAMIN, E. J. (1975), "Synthesis of cyclopropyl analogs of stilbene and stilbenediol as possible antiestrogens", Journal of Pharmaceutical Sciences, 64, 1626; STOBAUGH, J. F., MAGARIAN, R. A. AND PENTO, J. T. (1982), "Synthesis and biological evaluation of gem-dichlorocyclopropyl and cyclopropyl analogs of stilbene congeners as potential antiestrogens", Journal of Pharmaceutical Sciences, 71, 1126). Boron tribromide did not effect the deprotection of 8 and 16, and hence, aluminum chloride and n-BuSH (or EtSH) were used. Phenols 9 and 17 underwent gradual color changes when concentrated, and hence, were kept in solution and stored under nitrogen. The cis-acetate (10) of 9 was a stable light-yellow oil at 0° C. while the trans-isomer 18 was a crystalline solid.

Synthesis of 23 (FIG. 2) involved the phase-transfer dichlorocycloproponation of 1,1-bis-(p-methoxyphenyl) ethylene (22), which was produced from the Grignard reaction using p-methoxyphenyl magnesium bromide with ethyl acetate followed by the simultaneous dehydration of 21 with 5N $H_2SO_4$ (MIQUEL, J -F., WAHLSTAM, H., OLSSON, K. AND SUND-BECK, B. (1963), "Synthesis of unsymmetrical diphenylalkenes", Journal of Medicinal Chemistry, 6, 774). An improved method of demethylation was tried on 23 using iodotrimethylsilane reagent (Jung & Lyster, 1977; Jung & Lyster, 1980). Since the deprotection occurred much more slowly than with EtSH/$AlCl_3$, the organosilicon reagent offered the advantage of producing both 24 and 25 when the quantity of reagent and reaction time were controlled.

Bis-(p-methoxyphenyl)-cyclohexylidene methane 28 (FIG. 3) was prepared from methyl cyclohexane carboxylate 26 and p-methoxyphenyl magnesium bromide (Miquel et al., 1963). Dehydration of 27 was accomplished with a mixture of $H_2SO_4$ and acetic acid. While 29 was demethylated with iodotrimethylsilane in pyridine, 30 was difficult to isolate, and the demethylation was repeated using n-BuSH/$AlCl_3$. However, the best method found for demethylation involved the use of EtSH/$AlCl_3$ in $CH_2Cl_2$. EtSH has a lower boiling point than n-BuSH and offers the advantage of being easier to remove from the reaction mixture. Diphenol 30 underwent a gradual color change, but was obtained pure from the acid hydrolysis of the di-acetate 31.

Treatment of p-methoxydeoxybenzoic (32) (FIG. 4) with $PCl_5$ in refluxing benzene provided p-methoxy-α'-chlorostilbene 33 (Nagano, 1955), which underwent Friedel-Crafts conditions with anisole to furnish the triarylethylene 34. The carbonyl group in deoxybenzoic 32 was converted to a gem-dichloride intermediate, using phosphorus pentachloride, and with the subsequent elimination of HCl, the vinyl chloride 33 was obtained. Compound 32 was prepared using Friedel-Crafts conditions involving phenylacetyl chloride and anisole in carbon disulfide and aluminum chloride (BUCK, J. S. and IDE, W. S. (1932), "The isomeric desoxybenzanisoins", Journal of the American Chemical Society, 54, 3012). Demethylation of 35 was accomplished with EtSH/$AlCl_3$, and 36 was isolated by column chromatography. Drying of phenol 36 at a high temperature resulted in the formation of an indene, which was observed previously (MAGARIAN, R. A., MELTON, S. AND NATARELLI, G. (1972), "2-Chloro-1-phenylindene from 1,1-dichloro-trans-2,3-diphenylcyclopropane", Journal of Pharmaceutical Sciences, 61, 1216). Compound 36 was isolated as the diacetate (37) using column chromatography.

EXAMPLE 22

Biological Evaluation Methodology

The biological evaluation of the test compounds consisted of the in vitro rat cytosolic estradiol receptor binding assay, the in vivo immature mouse uterotrophic (estrogenic) and antiuterotrophic (antiestrogenic) assays, and the in vitro suppression of the proliferation of the EP positive MCF-7 human breast cancer cell line. Estradiol (pure agonist), TAM (agonist in mice and antagonist in MCF-7), MER 25 (pure antagonist) and Analog II (antagonist in mice) were used in the assays as standards.

Viral-free immature female Swiss-Webster mice were obtained at 17-19 days of age from Sasco weighing 8-10 g, and were used in the uterotrophic and antiuterotrophic assays. Immature female Sprague-Dawley rats, obtained at 17-19 days of age from Sasco, weighing 28-33 g, were used as sources of uteri for the estradiol receptor binding assay. Animals were housed in wire topped polycarbonate cages at six animals per cage, with the environment controlled at 25° C. and a 12 h light/dark cycle. The animals received a diet of Wayne Lab Blox rodent chow and tap water ad libitum.

Receptor Binding Assay

The RBAs of the test compounds were determined by the displacement of [$^3$H]-estradiol in vitro, as described previously (DAY, B. W., MAGARIAN, R. A., JAIN, P., PENTO, J. T., MOUSISSIAN, G. K. AND MEYER, K. L. (1991), "Synthesis and biological evaluation of a series of 1,1-dichloro-2,2,3-triarylcyclopropanes as pure antiestrogens", Journal of Medicinal Chemistry, 34, 842; KORENMAN, S. G. (1969), "Comparative binding affinity of estrogens and its relation to estrogenic potency", Steroid, 13, 163). Mature female Sprague-Dawley rats were ovariectomized at least two weeks prior to the receptor binding experiment. Each test compound was assayed at three concentrations in duplicate over a range of $10^{-3}$–$10^{-5}$M and $10^{-6}$–$10^{-8}$M for the estradiol standard. The nonspecific binding was determined by a parallel incubation of each compound with the addition of diethylstilbestrol to give a final concentration of $2 \times 10^{-5}$M DES which was sufficient to saturate all the estrogen receptors present in the cytosolic fraction. Specific displacement for each compound was determined by subtraction of nonspecific displacement from total displacement. The [$^3$H]-estradiol displacement curve for each test compound was determined by linear regression analysis and plotted graphically. The relative binding affinity for each compound was calculated (BLISS, C. I. (1967), "The statistics in biology", McGraw Hill, Inc: New York). Uterotrophic Assay for Estrogenic and Antiestrogenic Activity.

The assay for estrogenic activity was conducted as described previously (DAY, B. W., MAGARIAN, R. A., JAIN, P., PENTO, J. T., MOUSISSIAN, G. K. AND MEYER, K. L. (1991), "Synthesis and biological evaluation of a series of 1,1-dichloro-2,2,3-triarylcyclopropanes as pure antiestrogens", Journal of Medicinal Chemistry, 34, 842). Immature Swiss-Webster female mice (8-15 g) at 17-19 days of age were used. Estradiol was used in the dosage range of 0.01-0.04 μg (total dose) as the assay standard. Each cyclopropyl analogue was examined at doses of 5, 25, and 100 μg (total dose). Compounds 16 and 29 were tested at a total dose of 100, 250, 500 μg, and Compound 35 was retested at a total dose of 25, 100, 250 μg. Estrogenic activity was measured as an increase in uterine weight produced by each test compound.

The antiestrogenic assay was conducted as described for the estrogenic assay, except that each mouse in the cyclopropyl treatment groups received a standard stimulating dose of estradiol (0.03 μg) in sesame oil (0.1 mL) and the test compounds or MER 25 were administered in isopropyl myristate (0.05 mL) in a dosage range of 0.4, 0.8 and 1.6 mg (total dose). Isopropyl myristate was used to enhance the solubility of the test compounds, since it was determined to be nontoxic at the volume employed in the antiestrogenic assay. Antiestrogenic activity was measured as a decrease in the estradiol-stimulated antiuterotrophic response in groups that received both the test compound and estradiol as compared to the group treated only with estradiol.

In Vitro MCF-7 Human Breast Cell Cancer Line

MCF-7 (estrogen-receptor positive) human breast cancer cells (obtained from the Michigan Cancer Foundation, Detroit, Mich.) were grown at 37° C. in 75 cm$^2$ tissue culture (T-75) flasks, as monolayer cultures in RPMI 1640 phenol red-free media supplemented with 2 mM L-glutamine, gentamicin (50 μg/mL), penicillin (100 units/mL), streptomycin (100 μg/mL) and calf serum (5%). Cultures were grown in an incubator at 37° C. in a humid 5% CO$_2$ atmosphere, and fed on alternate days. Exponential growth was maintained by subculturing at eight day intervals when the cells per T-75 flask reached 10 to $12 \times 10^6$ cells. Cells were trypsinized, washed and plated in multiwell plates at a density of $5 \times 10^4$ cells/well in 3 mL of RPMI 1640 media. The cells were allowed to attach and were in logarithmic growth when the test compounds were added. The test compounds ($10^{-6}$M) in the presence or absence of a 10-fold lower dose of estradiol were dissolved in a polyethylene glycol 400: ethanol (55:45) mixture and added in the culture media in duplicate. Control samples received vehicle alone at the same concentration used in the treatment groups. The final concentration of the vehicle mixture was 0.1% of the incubation media. Cell growth was measured on alternate days using the hemocytometric trypan blue exclusion method. Percent inhibition of MCF-7 cells was calculated as the ratio of the control mean cell count per well minus the treatment group mean cell count per well to the control mean cell count per well, multiplied by 100.

Results

The biological evaluation of the test compounds are summarized in Table II.

TABLE II

Estrogen Receptor Binding Affinities[a] and Percent Inhibition of MCF-7 Human Breast Cancer Cells[b] of 1,1-Dichloro-2,2(3)-diaryl- and 2,2,3-triarylcyclopropanes.

| Compound | RBA[c], % | MCF-7 Inhibition[b], % |
|---|---|---|
| Tamoxifen[d] | 0.87 | 25.6 |
| Analog II[d] | 0.01 | 20.4 |
| MER-25[d] | —[e] | nd[f] |
| 8 | —[e] | 25.3 |
| 10 | 0.07 | 32.0 |
| 14 | 0.01 | 37.0 |
| 16 | —[e] | —[g] |
| 18 | 0.25 | —[g] |
| 23 | —[e] | 30.0 |
| 24 | 0.02 | —[g] |
| 25 | 0.04 | —[g] |
| 29 | —[e] | 37.0 |
| 30 | 0.62 | 21.3 |
| 31 | 0.05 | —[g] |
| 35 | —[e] | —[g] |

TABLE II-continued

Estrogen Receptor Binding Affinities[a] and Percent Inhibition of MCF-7 Human Breast Cancer Cells[b] of 1,1-Dichloro-2,2(3)-diaryl- and 2,2,3-triarylcyclopropanes.

| Compound | RBA[c], % | MCF-7 Inhibition[b], % |
|---|---|---|
| 37 | 0.08 | —[g] |

[a]Determined by competitive radiometric binding assay with rat uterine cytosol as a source of receptor, [³H]estradiol as tracer, and dextran-coated charcoal as absorbant for free ligand.

[b]% MCF-7 inhibition was calculated as follows:

$$\frac{\text{(mean cell count per well in control group)} - \text{(mean cell count per well in treatment groups)}}{\text{(mean cell count per well in the control group)}} \times 100$$

[c]Binding affinities are expressed relative to that of estradiol = 100% (RBA = relative binding affinity) and are the average of duplicate determinations minus non-specific binding.
[d]Day, B. W. et al, J. Med. Chem. 34, 842-851 (1991),
[e]Less than 0.01%.
[f]Not determined.
[g]Less than 10%.

Receptor Binding Assay

The relative binding affinities (RBAs), as determined by the competitive radiometric binding assay and measured by [³H]-estradiol displacement from the ovariectomized rat uterine cytosolic estrogen receptor preparation, after subtracting non-specific receptor binding, were calculated for all of the synthesized target compounds, TAM, MER 25, Analog II, and estradiol. The displacement curves were plotted as percent receptor-bound [³H]-estradiol versus concentration of test compounds (not shown) and the receptor binding affinity of each compound is presented in Table II.

Tamoxifen produced a displacement curve which was parallel to estradiol and had a RBA of 0.87% of estradiol (Day et al., 1991). Most other compounds demonstrated a very weak dose-related displacement of [³H]-estradiol from the estrogen receptor (Table II), including the antiestrogen MER-25. The highest relative binding affinity, 0.62% of estradiol, was exhibited by Compound 30 (comparable to tamoxifen), followed by the trans-acetate Compound 18 (0.25% of estradiol). The methyl ethers, Compounds 8, 14, 16, 23, 29, and 35 had dose-dependent displacement curves with shallower slopes than their acetoxy and phenolic analogues (not shown). The cis-methoxy Compound 8 has the lowest RBA and the bisphenol Compound 30, the highest.

Uterotrophic Assay

Figure 8:
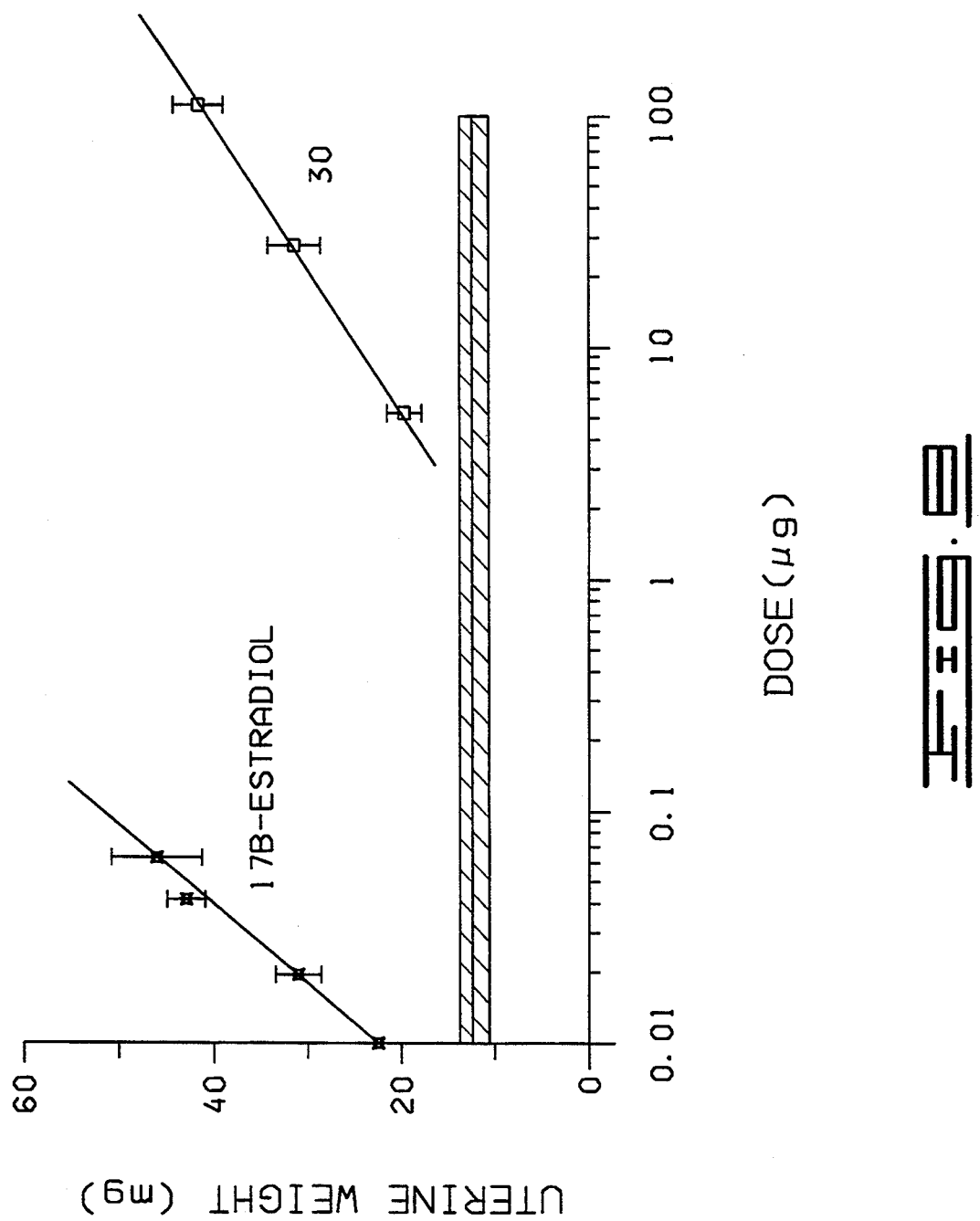
FIG. 8 is a graph comparing the estrogenic activity of Compound 30 as compared to estradiol. Each point represents the mean±SEM for each dosage group. The hatched bar represents the mean±SEM of the not-treated control group.

Compound 30 is the only one in the series which produced a dose-dependent increase in uterine weight at doses of 5, 25, and 100 μg (FIG. 8), and whose relative potency was found to be 0.05% of that of estradiol. The responses of Compounds 8, 23, 25, 31 and 37 from all three doses (5, 25 & 100 μg) are well below the control group. Compounds 16, 29, and 35 produced a slight increase in uterine weight at doses of 25 and 100 μg. Therefore, Compounds 16 and 29 were retested at 100, 250, and 500 μg, while Compound 35 was retested at 25, 100, and 250 μg. However, no significant uterotrophic responses were observed.

Antiuterotrophic Assay

All compounds were tested for their ability to antagonize the uterine weight gain in immature mice. None of the compounds displayed any significant antiestrogenic activity in the three-day immature mouse assay at doses of 0.4, 0.8, and 1.6 mg; however, MER 25 produced a significant reduction in estradiol-induced uterotrophic activity over the same dosage range. In addition to being devoid of antiestrogenic activity, only Compound 30 augmented uterotrophic effects beyond the stimulating dose of estradiol. In a separate antiestrogen experiment in which a lower stimulating dose (0.02 μg) of estradiol was used, 30 exhibited a similar degree of augmentation.

Cell Culture Assay

Thirteen compounds, Analog II, TAM, and MER 25 were tested for their antiproliferative activity in the MCF-7 human breast cancer cell line (Table II). Compounds were tested at a concentration of $10^{-6}$M in the presence or absence of $10^{-7}$M estradiol to assess their ability to alter the growth of the cells (Table II). The $10^{-6}$M concentration was selected since it was reported that the inhibition of the MCF-7 cells by antiestrogens and TAM occurred either at that concentration or less, and were both selective and estrogen receptor specific. Concentrations of antiestrogens greater than $5 \times 10^{-6}$M were reported to have nonspecific cytotoxic effects (BRIAND, P. AND LYKKESFELDT, A. E. (1984), "Effect of estrogen and antiestrogen on the human breast cancer cell line MCF-7 adapted to growth at low serum concentration", Cancer Research, 44, 1114).

Three derivatives (Compounds 8, 10, 14) of the lead compound, Analog II, inhibited cell growth, while the trans isomers (Compounds 16, 18) did not. Of the 1,1-dichloro-2,2-bis-diaryl-cyclopropanes (Compounds 23, 24, 25) only 23 inhibited cell growth. In the cyclopropyl analogues of cyclofenil (Compounds 29, 30, 31), the dimethoxy and dihydroxy derivatives (Compounds 29, 30) were active inhibitors of cell growth, while the diacetoxy Compound 31 was not. Similarly, the 2,2,3-triarylcyclopropanes (Compounds 35, 37) did not alter cell growth.

Only the growth inhibition produced by Compound 30 (FIG. 9) was reversed by $10^{-7}$M estradiol, which also enhanced estradiol-induced cell growth above the control. The mean inhibition of MCF-7 cell growth over 6 days ranged from 20 to 37% (Table II).

All references cited herein including patents, pending patent applications and publications are hereby incorporated herein by reference.

Changes may be made in the embodiments of the invention described herein or in parts of the elements of the embodiments described herein of in the steps or in the sequence of steps of the methods described herein without departing from the spirit and scope of the invention as defined in the following claims.

What is claimed is:

1. A cyclopropane compound having the formula:

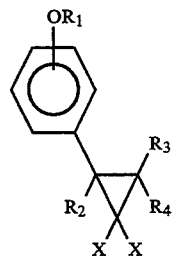

or any pharmaceutically acceptable salt thereof, in which

X is a halogen atom;

$R_1$ is a hydrogen;

$R_2$ is a hydroxyphenyl; and $R_3$ is a cyclopentyl group having the first position carbon and the fifth position carbon bonded to the same carbon of the cyclopropane wherein the $R_4$ group is absent.

2. The compound of claim 1 in which X is chlorine.

3. A composition of matter comprising a compound having the formula:

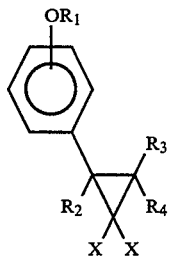

or any pharmaceutically acceptable salt thereof and a pharmaceutically acceptable carrier of sufficient quantity to solubilize the compound, in which:

X is a halogen atom;

$R_1$ is a hydrogen;

$R_2$ is a hydroxyphenyl; and $R_3$ is a cyclopentyl group having the first position carbon and the fifth position carbon bonded to the same carbon of the cyclopropane wherein the $R_4$ group is absent.

4. A method of increasing uterine growth in a mammal comprising administering to the mammal an effective amount of one or more of the compounds having the formula:

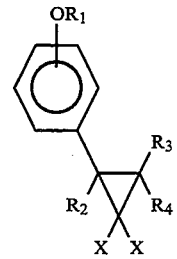

or any pharmaceutically acceptable salt thereof, in which

X is a halogen atom;

$R_1$ is a hydrogen;

$R_2$ is a hydroxyphenyl; and $R_3$ is a cyclopentyl group having the first position carbon and the fifth position carbon bonded to the same carbon of the cyclopropane.

5. The method of claim 4 in which X is chlorine.

6. The method of claim 4 wherein the compound further comprises a pharmaceutically acceptable carrier of sufficient quantity to solubilize the compound.

* * * * *

UNITED STATES PATENT AND TRADEMARK OFFICE
CERTIFICATE OF CORRECTION

PATENT NO.　:　5,397,802

DATED　　　:　March 14, 1995

INVENTOR(S):　Magarian et al.

It is certified that error appears in the above-identified patent and that said Letters Patent is hereby corrected as shown below:

Column 1, line 21, please delete "06/363/429" and substitute therefor -- 06/363,429 --.

Column 1, line 51, please delete "salts" and substitute therefor -- salt --.

Column 8, line 53, please delete "phenyl" and substitute therefor -- benzyl --.

Column 10, line 21, please delete "b" and substitute therefor -- by --.

Column 11, lines 17-18, please delete "recrystallized" and substitute -- crystallized --.

Column 16, line 24, please delete "17)" and substitute therefor -- (17) --.

Column 16, Table I, No. column, please delete "21" and substitute therefor -- 24 --.

Column 16, Table I, formula column, second entry, please delete "$C_7H_{14}Cl_2O$" and substitute therefor -- $C_{17}H_{14}Cl_2O$ --.

Column 16, Table I, formula column, third entry, please delete "$C_{27}H_{10}Cl_2O_2$" and substitute therefor -- $C_{17}H_{10}Cl_2O_2$ --.

UNITED STATES PATENT AND TRADEMARK OFFICE
CERTIFICATE OF CORRECTION

PATENT NO. : 5,397,802
DATED : March 14, 1995
INVENTOR(S) : Magarian et al.

It is certified that error appears in the above-identified patent and that said Letters Patent is hereby corrected as shown below:

Column 18, line 38, please delete "p-methoxydeoxybenzoic" and substitute therefor -- p-methoxydeoxybenzoin --.

Column 18, line 42, please delete "deoxybenzoic" and substitute therefor -- deoxybenzoin --.

Column 19, line 1, please delete "EP" and substitute therefor -- ER --.

Column 19, lines 46-47, "Uterotrophic Assay for Estrogenic and Antiestrogenic Activity" should be set apart and centered as a heading.

Signed and Sealed this

Eleventh Day of July, 1995

Attest:

BRUCE LEHMAN

Attesting Officer

Commissioner of Patents and Trademarks